(12) United States Patent
Ito

(10) Patent No.: US 9,448,157 B2
(45) Date of Patent: Sep. 20, 2016

(54) MICROPARTICLE SORTING APPARATUS, MICROCHIP FOR SORTING MICROPARTICLES AND MICROPARTICLE SORTING METHOD

(71) Applicant: Sony Corporation, Tokyo (JP)

(72) Inventor: Tatsumi Ito, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/413,543

(22) PCT Filed: May 31, 2013

(86) PCT No.: PCT/JP2013/065176
§ 371 (c)(1),
(2) Date: Jan. 8, 2015

(87) PCT Pub. No.: WO2014/013802
PCT Pub. Date: Jan. 23, 2014

(65) Prior Publication Data
US 2015/0204774 A1 Jul. 23, 2015

(30) Foreign Application Priority Data
Jul. 18, 2012 (JP) .................. 2012-159606

(51) Int. Cl.
*B07C 5/34* (2006.01)
*G01N 15/14* (2006.01)
(Continued)

(52) U.S. Cl.
CPC ....... *G01N 15/1484* (2013.01); *B01L 3/50273* (2013.01); *B01L 3/502761* (2013.01); *G01N 15/147* (2013.01); *B01L 2200/0652* (2013.01); *B01L 2300/0627* (2013.01); *B01L 2300/0816* (2013.01); *B01L 2300/0877* (2013.01); *B01L 2400/0415* (2013.01); *B01L 2400/0481* (2013.01); *B01L 2400/0487* (2013.01); *B01L 2400/0622* (2013.01); *B07C 5/34* (2013.01);
(Continued)

(58) Field of Classification Search
CPC . B07C 5/342; B07C 5/3425; B01L 3/50273; B01L 3/502761; B01L 3/502792; B01L 2200/0652; B01L 2300/0861; B01L 2300/0864; B01L 2300/0877; B01L 2300/14; B01L 2400/0475; B01L 2400/0487; G01N 15/1484; G01N 2015/149
See application file for complete search history.

(56) References Cited

U.S. PATENT DOCUMENTS

| 4,936,465 A | * | 6/1990 | Zold | ........................ B07C 3/02 209/3.1 |
| 5,837,200 A | * | 11/1998 | Diessel | ............ B01L 3/502761 209/155 |
| 7,258,774 B2 | * | 8/2007 | Chou | .................. B01L 3/50273 204/450 |

(Continued)

FOREIGN PATENT DOCUMENTS

| JP | 01-170853 A | 7/1989 |
| JP | 2004-113223 A | 4/2004 |

(Continued)

*Primary Examiner* — Joseph C Rodriguez
(74) *Attorney, Agent, or Firm* — Chip Law Group

(57) ABSTRACT

There is provided a microparticle sorting apparatus including a main channel through which a fluid including microparticles flows, a branch channel that is in communication with the main channel, an actuator that causes a negative pressure to be generated in the branch channel, and a drive unit that controls a voltage applied to the actuator to cause a change in pressure containing a step waveform component and an undershoot waveform component in the branch channel.

15 Claims, 17 Drawing Sheets

(51) Int. Cl.
*B01L 3/00* (2006.01)
*G01N 15/10* (2006.01)

(52) U.S. Cl.
CPC . *G01N 2015/1006* (2013.01); *G01N 2015/149* (2013.01)

(56) References Cited

U.S. PATENT DOCUMENTS

| | | | | |
|---|---|---|---|---|
| 7,452,725 | B2* | 11/2008 | Leary | G01N 15/14 422/504 |
| 8,487,273 | B2* | 7/2013 | Ito | B01L 3/502761 250/458.1 |
| 8,609,039 | B2* | 12/2013 | Zhou | B01L 3/5025 422/500 |
| 8,623,294 | B2* | 1/2014 | Asogawa | B01L 3/50273 422/50 |
| 9,018,556 | B2* | 4/2015 | Ito | B07C 5/3416 209/576 |
| 2006/0180517 | A1* | 8/2006 | Frazier | G01N 15/1459 209/579 |
| 2008/0213821 | A1* | 9/2008 | Liu | B01L 3/502761 435/39 |
| 2010/0006441 | A1* | 1/2010 | Renaud | B01L 3/502746 204/643 |
| 2011/0030808 | A1* | 2/2011 | Chiou | B01L 3/502738 137/13 |
| 2011/0207238 | A1* | 8/2011 | Horii | B01L 3/50273 436/518 |
| 2011/0271746 | A1 | 11/2011 | Shinoda et al. | |
| 2012/0153185 | A1 | 6/2012 | Ito et al. | |
| 2013/0083315 | A1* | 4/2013 | Lo | G01J 3/46 356/73 |
| 2013/0118905 | A1* | 5/2013 | Morimoto | B01L 3/502761 204/643 |
| 2013/0256200 | A1* | 10/2013 | Ito | B07C 5/3422 209/552 |
| 2014/0087412 | A1* | 3/2014 | Fouras | B01L 3/502761 435/29 |
| 2015/0298122 | A1* | 10/2015 | Zeng | B01L 3/50273 435/309.1 |

FOREIGN PATENT DOCUMENTS

| | | |
|---|---|---|
| JP | 2005-538727 A | 12/2005 |
| JP | 2009-100698 A | 5/2009 |
| JP | 2011-237201 A | 11/2011 |
| JP | 2012-127922 A | 7/2012 |

* cited by examiner

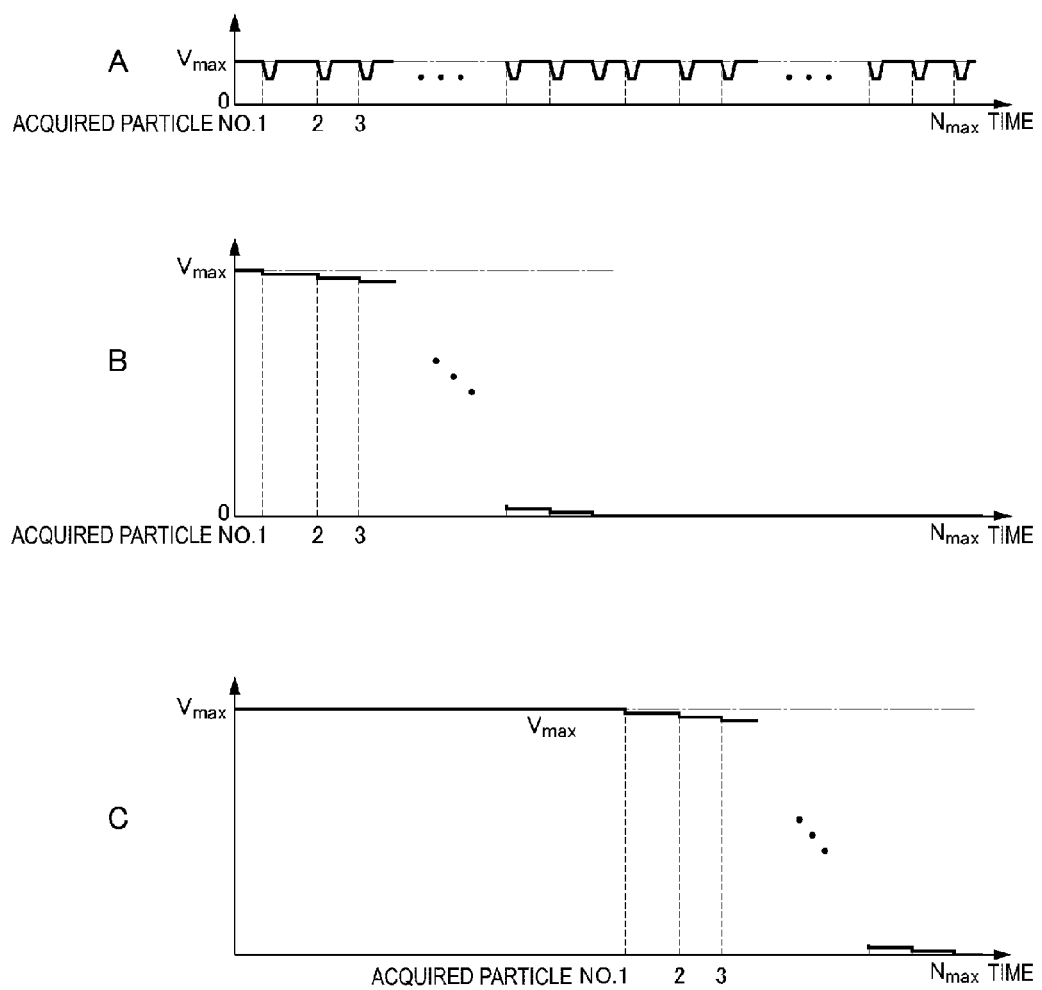

MICROPARTICLE SORTING APPARATUS, MICROCHIP FOR SORTING MICROPARTICLES AND MICROPARTICLE SORTING METHOD

TECHNICAL FIELD

The present technology relates to a microparticle sorting apparatus, a microchip for sorting microparticles and a microparticle sorting method. More specifically, the present technology relates to a microparticle sorting apparatus that separates and recovers only target microparticles from the microparticles that are flowing along a channel.

BACKGROUND ART

A microparticle sorting apparatus that forms a microparticle-containing sheath flow in a channel, detects fluorescence and scattered light emitted from the microparticles by irradiating light on the microparticles in the sheath flow, and separates and recovers a microparticle group (population) that exhibits a predetermined optical characteristic is known. For example, in a flow cytometer, a specific type of cell only is separated and recovered by labeling a plurality of types of cell included in a sample with a fluorescent dye and optically identifying the fluorescent dye labeled on each cell.

In Patent Literature 1 and Patent Literature 2, microchip-type microparticle sorting apparatuses are disclosed that perform analysis by forming a sheath flow in a channel formed on a microchip that is made from plastic, glass or the like.

The microparticle sorting apparatus disclosed in Patent Literature 1 controls the feeding direction of the sheath flow at a branching portion between an introduction channel in which the sheath flow is formed and a branch channel in communication with the introduction channel by generating an air bubble based on laser irradiation at the branching portion. According to this microparticle sorting apparatus, controlling the feeding direction of the sheath flow at the branching portion with an air bubble enables just the target microparticles to be collected into the branch channel from the introduction channel and sorted.

Further, the microfluidic system disclosed in Patent Literature 2 sorts target microparticles by using an actuator to control the feeding direction of a sheath flow at a channel branching portion. In this microfluidic system, the actuator changes the feeding direction of the sheath flow by pressing against a chamber that is connected to a branching portion between an introduction channel in which the sheath flow is formed and a branch channel in communication with the introduction channel to push out fluid in the chamber.

CITATION LIST

Patent Literature

Patent Literature 1: JP 2009-100698A
Patent Literature 2: JP 2005-538727T

SUMMARY OF INVENTION

Technical Problem

For microchip-type microparticle sorting apparatuses, in order to further increase the speed and accuracy of analysis, there is a demand for a technology for rapidly and stably extracting only target microparticles from a sheath flow that is flowing through a channel.

According to an embodiment of the present technology, there is provided a microparticle sorting apparatus that can rapidly and stably extract only target microparticles from a sheath flow that is flowing through a channel.

Solution to Problem

So as to solve the problem, according to the present technology, there is provided a microparticle sorting apparatus including a main channel through which a fluid including microparticles flows, a branch channel that is in communication with the main channel, an actuator that causes a negative pressure to be generated in the branch channel, and a drive unit that controls a voltage applied to the actuator to cause a change in pressure containing a step waveform component and an undershoot waveform component in the branch channel.

In this microparticle sorting apparatus, the negative pressure derived from the step waveform component enables the fluid having a volume necessary for drawing in the microparticles to be collected into the branch channel. At the same time, the large negative pressure derived from the undershoot waveform component enables an operation of drawing in the microparticles into the branch channel to become faster.

In the microparticle sorting apparatus according to an embodiment of the present technology, the voltage of the undershoot-step waveform can be applied to the actuator, so as to generate a change in pressure containing the step waveform component and the undershoot waveform component.

Alternatively, two or more of the actuators can be disposed, so that the drive unit applies the voltage of the pulse waveform to one or more of the actuators, while applying the voltage of the step waveform to other one or more of the actuators. This can also generate the change in pressure containing the step waveform component and the undershoot waveform component. In this case, when the pressure chambers are arranged in series in the branch channel, the actuator to be applied with the voltage of the pulse waveform is arranged corresponding to the pressure chamber that is located closer to a communication opening to the main channel, than the actuator to be applied with the voltage of the step waveform or the undershoot-step waveform. In addition, the actuator to be applied with the voltage of the pulse waveform may be arranged on one surface of the microchip, and the actuator to be applied with the voltage of the step waveform or the undershoot-step waveform may be arranged on the opposite surface, with respect to one of the pressure chamber.

In the microparticle sorting apparatus according to an embodiment of the present technology, the main channel and the branch channel are formed inside a microchip. Also, the actuator is arranged in contact with the surface of the microchip at a position corresponding to the branch channels, and provide displacement to the contact surface of the microchip.

With regard to the microparticle sorting apparatus according to the present technology, a portion of the branch channel corresponding to an arrangement position of the actuator may be configured as a pressure chamber where a change in volume is caused by the displacement.

In addition, according to the present technology, there is provided a microchip for sorting microparticles. A main channel through which a fluid including microparticles flows, and a branch channel that is in communication with the main channel are formed inside the microchip, and an actuator that provides displacement on a contact surface is arranged in contact with a surface at a position corresponding to the branch channel.

In the microchip for sorting microparticles according to an embodiment of the present technology, the branch channel may include a pressure chamber where the change in volume is caused by the displacement.

Also, in the microchip for sorting microparticles according to an embodiment of the present technology, a plurality of combinations of the pressure chamber and the actuator may be disposed, or the actuators may be respectively arranged on one surface and the opposite surface of the microchip with respect to one of the pressure chamber.

In addition, according to the present technology, there is provided a microparticle sorting method, including a procedure of generating a negative pressure within a branch channel that is in communication with a main channel, to draw, into the branch channel, microparticles included in a fluid that flows through the main channel. In the procedure, a change in pressure containing a step waveform component and an undershoot waveform component is caused within the branch channel.

In the microparticle sorting method according to an embodiment of the present technology, the change in pressure can be caused by the undershoot-step waveform.

In an embodiment of the present technology, the term "microparticle" has a broad meaning that includes biologically-relevant microparticles such as cells, microbes, ribosomes and the like, as well as synthetic particles such as latex particles, gel particles, industrial particles and the like.

Examples of biologically-relevant microparticles include the chromosomes, liposomes, mitochondria, organelles (cell organelles) that form various cells. Examples of cells include animal cells (hematopoietic cells etc.) and plant cells. Examples of microbes include bacteria such as *E. coli*, viruses such as tobacco mosaic virus, fungi such as yeast and the like. Further example of biologically-relevant microparticles includes nucleic acids, proteins, complexes of these and the like. Examples of industrial particles include organic or inorganic polymer materials, metals and the like. Examples of organic polymer materials include polystyrene, styrene-divinyl benzene, poly methyl methacrylate and the like. Examples of inorganic polymer materials include glass, silica, magnetic materials and the like. Examples of metals include metal colloids, aluminum and the like. Although the shape of these microparticles is usually spherical, the microparticles may also have a non-spherical shape. Further, the size and mass of these microparticles is not especially limited.

Advantageous Effects of Invention

According to the embodiments of the present technology described above, a microparticle sorting apparatus is provided that can rapidly and stably extract only target microparticles from a sheath flow that is flowing through a channel.

BRIEF DESCRIPTION OF DRAWINGS

FIG. 3 is a diagram illustrating a configuration of the microchip 1a.

FIG. 4 is a diagram illustrating a configuration of the microchip 1a.

FIG. 5 is a diagram illustrating a configuration of a branching portion between a main channel 15 and a sorting channel 16 of the microchip 1a.

FIG. 18 is a diagram illustrating voltages of a "pulse waveform" (A) to be applied to an actuator 32, a "step waveform" (B) to be applied to an actuator 31, and a "step waveform" to be applied to an actuator 33, from a drive unit 23 of the microparticle sorting apparatus D.

DESCRIPTION OF EMBODIMENTS

Hereinafter, preferred embodiments of the present technology will be described with reference to the appended drawings. It is noted that the embodiments described below are examples of a representative embodiment of the present technology, and do not permit the scope of the present technique to be narrowly interpreted. The description will be made in the order below.

1. Configuration of the microparticle sorting apparatus and the microchip for sorting microparticles according to the first embodiment
[Whole configuration of apparatus]
[Microchip configuration]
2. Operation of the microparticle sorting apparatus according to the first embodiment
[Sorting operation]
[Drive signal]
3. Configuration of the microparticle sorting apparatus and the microchip for sorting microparticles according to the second embodiment
[Microchip configuration]
[Whole configuration of apparatus]
4. Operation of the microparticle sorting apparatus according to the second embodiment
[Drive signal]
5. Configuration of the microparticle sorting apparatus and the microchip for sorting microparticles according to the third embodiment
[Microchip configuration]
[Whole configuration of apparatus]
6. Operation of the microparticle sorting apparatus according to the third embodiment
[Drive signal]
7. Configuration of the microparticle sorting apparatus and the microchip for sorting microparticles according to the fourth embodiment
[Microchip configuration]
[Whole configuration of apparatus]
8. Operation of the microparticle sorting apparatus according to the fourth embodiment
[Drive signal]
9. Microparticle sorting method and microparticle sorting program 1. Configuration of the Microparticle Sorting Apparatus and the Microchip for Sorting Microparticles According to the First Embodiment

[Whole Configuration of Apparatus]

Figure 1:
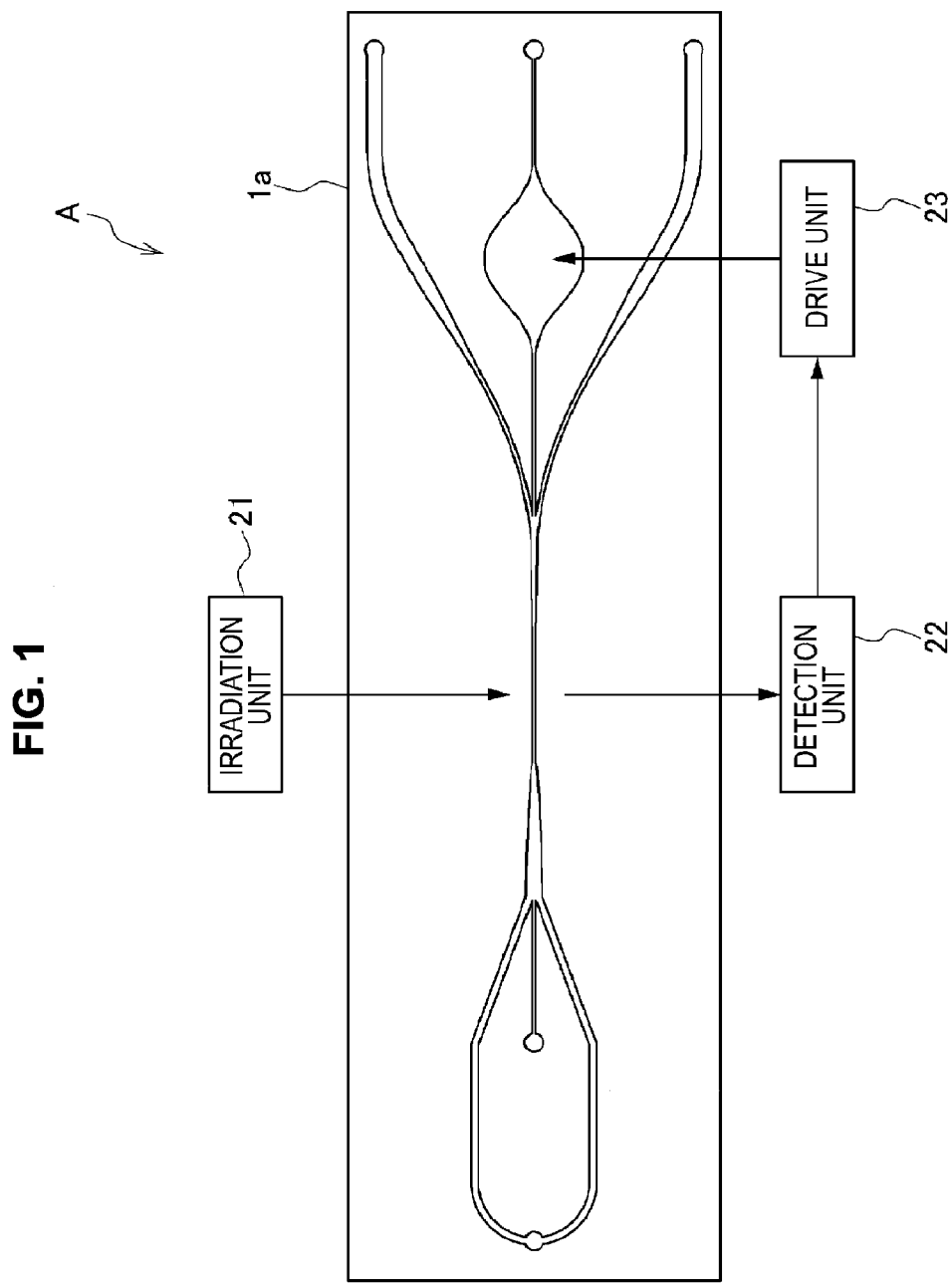
FIG. 1 is a diagram illustrating a configuration of a microparticle sorting apparatus A according to a first embodiment of the present technology.
Figure 2:
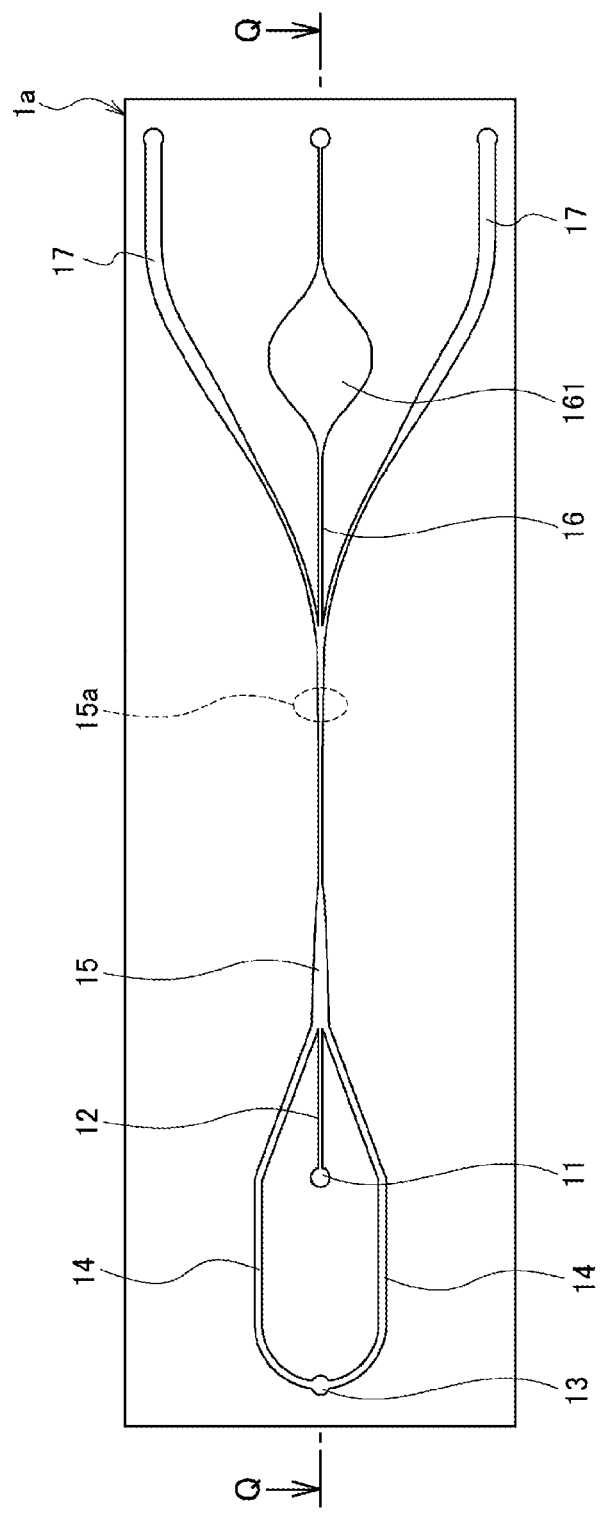
FIG. 2 is a diagram illustrating a configuration of a microchip 1a that is mounted on a microparticle sorting apparatus A.
Figure 3:
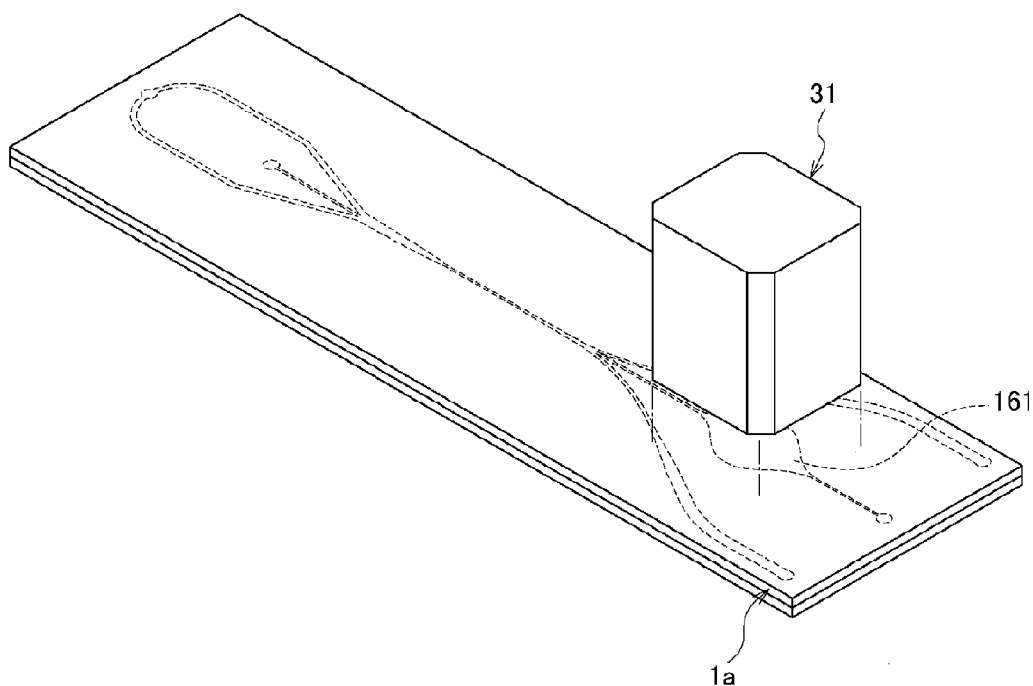
Figure 4:
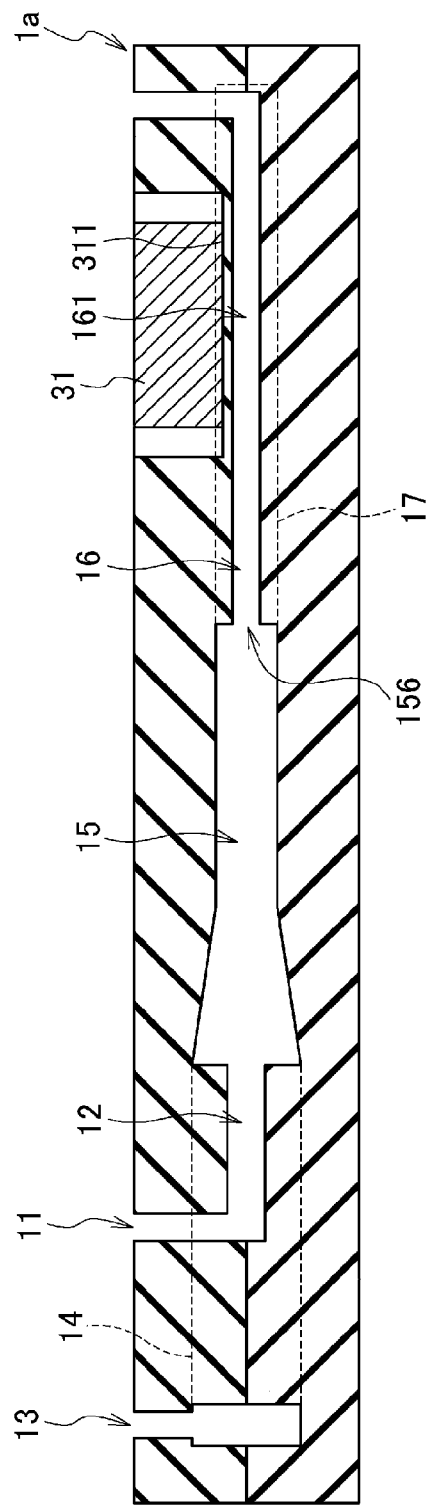

FIG. 1 is a diagram illustrating a configuration of a microparticle sorting apparatus A according to a first embodiment of the present technology. Also, FIG. 2 to FIG. 4 are each a diagram illustrating a configuration of a microchip that is mounted on the microparticle sorting apparatus A. FIG. 2 is a top view; FIG. 3 is a perspective view; and FIG. 4 is a cross-sectional view corresponding to the Q-Q cross section in FIG. 2.

The microparticle sorting apparatus A includes a microchip 1a, an irradiation unit 21, a detection unit 22, and a drive unit 23. In the microchip 1a is formed a main channel 15 through which a fluid (sample fluid) including microparticles that are the target of analysis flows (refer to FIG. 2). Further, an actuator 31 is arranged on the surface of the microchip 1a (refer to FIG. 3).

The irradiation unit 21 irradiates light (excitation light) on the microparticles flowing through the main channel 15 in the microchip 1a. The irradiation unit 21 includes, for example, a light source that emits excitation light and an objective lens that focuses the excitation light on the microparticles flowing through the main channel 15. The light source may be appropriately selected based on the analysis objective from among a laser diode, a SHG laser, a solid laser, a gas laser, a high luminance LED and the like. The irradiation unit 21 can optionally also have optical elements other than the light source and the objective lens.

The detection unit 22 detects fluorescence and scattered light that are emitted from the microparticles due to the irradiation with excitation light. The detection unit 22 includes an objective lens, which focuses the fluorescence and scattered light emitted from the microparticles, a detector and the like. As the detector, a PMT, a photodiode, a CCD, and a CMOS can be used. The detection unit 22 may optionally also have optical elements other than the objective lens and the detector.

The fluorescence that is detected by the detection unit 22 may be fluorescence emitted from the microparticles themselves or fluorescence emitted from a fluorescent substance that is labeled on the microparticles. Further, the scattered light that is detected by the detection unit 22 may be various types of scattered light, such as forward scattered light, side scattered light, Rayleigh scattered light, and Mie scattering.

The fluorescence and scattered light detected by the detection unit 22 are converted into an electric signal, and the electric signal is output to the drive unit 23. The drive unit 23 determines the optical characteristics of the microparticles based on the input electric signal. Further, the drive unit 23 has a function for collecting microparticles that have been determined to satisfy a predetermined characteristic from the main channel 15 in a sorting channel 16 by applying a voltage to the actuator 31 and controlling that voltage. This function of the drive unit 23 will be described in more detail below. The drive unit 23 is configured from a hard disk in which programs and an OS for executing the below-described various processes are stored, a CPU, a memory and the like.

[Microchip Configuration]

The configuration of the microchip 1a will now be described in more detail with reference to FIGS. 2 to 4. A sample fluid that includes microparticles is introduced from a sample fluid inlet 11 into a sample fluid channel 12. Further, a sheath fluid is introduced from a sheath fluid inlet 13. The sheath fluid introduced from the sheath fluid inlet 13 is split and fed into two sheath fluid channels 14 and 14. The sample fluid channel 12 and the sheath fluid channels 14 and 14 merge to form the main channel 15. A sample fluid laminar flow fed through the sample channel 12 and a sheath fluid laminar flow fed through the sheath fluid channels 14 and 14 merge in the main channel 15, and form a sheath flow in which the sample fluid laminar flow is sandwiched by the sheath fluid laminar flow (refer to FIG. 5C described later).

Reference numeral 15a in the figure denotes a detection area where excitation light is irradiated by the irradiation unit 21 and fluorescence and scattered light are detected by the detection unit 22. The microparticles are fed to the detection area 15a in a single line arranged in the sheath flow formed in the main channel 15, and are irradiated with the excitation light from the irradiation unit 21.

Figure 5:
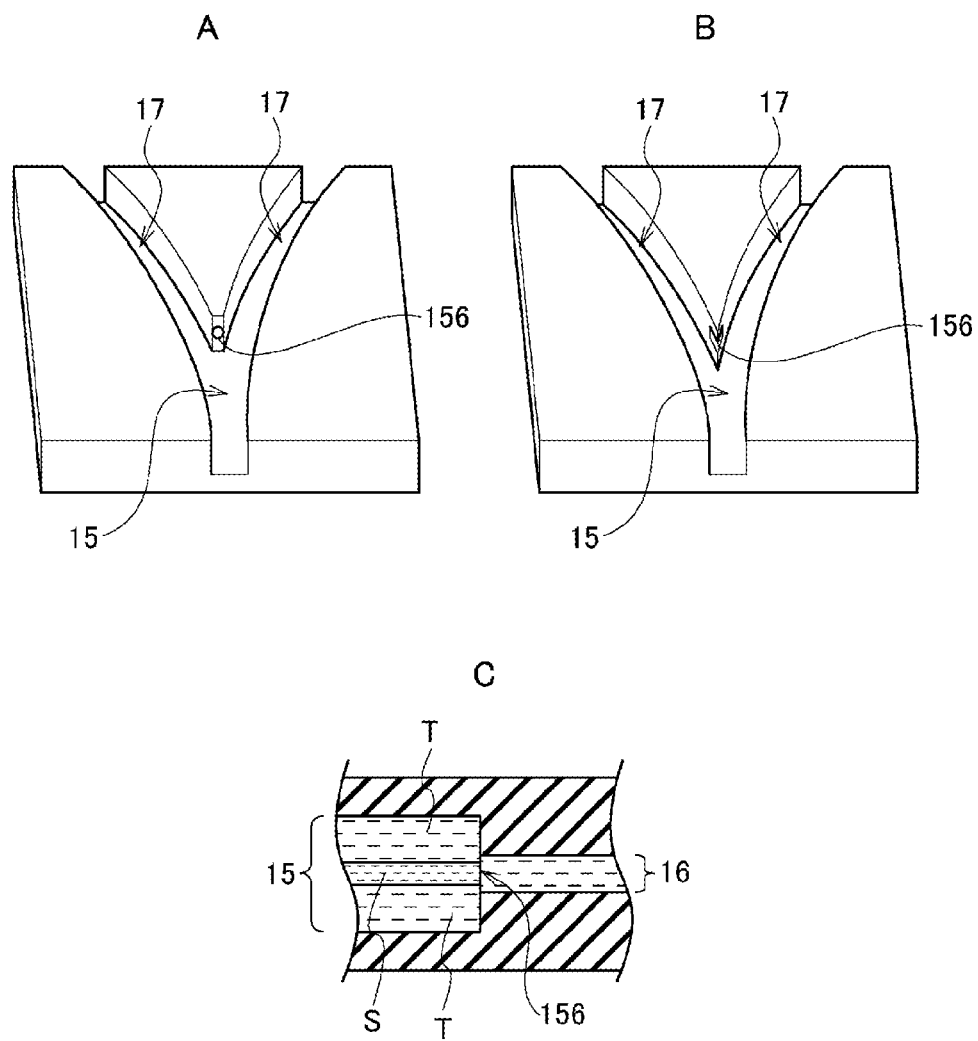

The main channel 15 splits into three channels downstream from the detection area 15a. A configuration of the branching portion of the main channel 15 is illustrated in FIG. 5. Downstream from the detection area 15a, the main channel 15 is in communication with three branch channels, the sorting channel 16 and waste channels 17 and 17. Of these, the sorting channel 16 is a channel into which microparticles that have been determined by the drive unit 23 to satisfy a predetermined optical characteristic (hereinafter referred to as "target particles") are collected. On the other hand, microparticles that are determined by the drive unit 23 as not satisfying the predetermined optical characteristic (hereinafter referred to as "non-target particles") are not collected in the sorting channel 16, and flow into either of the two waste channels 17 and 17.

The collecting of the target particles into the sorting channel 16 is performed by generating a negative pressure in the sorting channel 16 with the actuator 31 to suck the sample fluid including the target particles and the sheath fluid into the sorting channel 16. The actuator 31 is a piezo element or similar device. The actuator 31 is arranged in contact with the surface of the microchip 1*a*, at a position corresponding to the sorting channel 16. More specifically, the actuator 31 is arranged at a position corresponding to a pressure chamber 161 that is provided in the sorting channel 16 as an area whose inner space has expanded (refer to FIGS. 3 and 4).

The actuator 31 causes the pressure in the sorting channel 16 to change via the surface (contact face) of the microchip 1*a* by producing a stretching force due to a change in the applied voltage. When a flow is produced in the sorting channel 16 due to a change in the pressure in the sorting channel 16, the volume of the sorting channel 16 simultaneously changes too. The volume of the sorting channel 16 changes until it reaches a volume that is stipulated based on the displacement of the actuator 31 corresponding to the applied voltage. More specifically, when a voltage has been applied and the sorting channel 16 is in a stretched state, the actuator 31 keeps the volume of the pressure chamber 161 small by pressing against a displacement plate 311 forming the pressure chamber 161 (refer to FIG. 4). When the applied voltage decreases, the actuator 31 generates a force in a contracting direction, whereby the pressing against the displacement plate 311 weakens and a negative pressure is generated in the pressure chamber 161.

In order to efficiently transmit the stretching force of the actuator 31 into the pressure chamber 161, as illustrated in FIG. 4, it is preferred to form a recess on the surface of the microchip 1*a* at the position corresponding to the pressure chamber 161, and arrange the actuator 31 in this recessed portion. Consequently, the displacement plate 311 that serves as the contact face of the actuator 31 can be made thinner, so that the displacement plate 311 can be easily displaced by changes in the pressing force generated by expansion and contraction of the actuator 31, allowing the volume of the pressure chamber 161 to change.

In FIGS. 4 and 5, reference numeral 156 denotes a communication opening of the sorting channel 16 to the main channel 15. The target particles being fed in the sheath flow formed in the main channel 15 are collected in the sorting channel 16 from the communication opening 156.

To facilitate the collection of the target particles in the sorting channel 16 from the main channel 15, as illustrated in FIG. 5C, it is desirable to form the communication opening 156 so as to open onto a position corresponding to a sample fluid laminar flow S in the sheath flow formed in the main channel 15. The shape of the communication opening 156 is not especially limited, and may be, for example, a flat opening shape like that illustrated in FIG. 5A, or a notched opening shape like that illustrated in FIG. 5B formed by cutting the channel walls of the two waste channels 17.

The microchip 1*a* can be configured by laminating a substrate layer on which the main channel 15 and the like are formed. The formation of the main channel 15 and the like on the substrate layer can be carried out by injection molding of a thermoplastic resin using a mold. Examples of thermoplastic resins that can be used include plastics that are known as related-art microchip materials, such as polycarbonate, polymethyl methacrylate resin (PMMA), cyclic polyolefins, polyethylene, polystyrene, polypropylene, and polydimethylsiloxane (PDMS).

2. Operation of the Microparticle Sorting Apparatus According to a First Embodiment of the Present Technology

[Sorting Operation]

Next, the operation of the microparticle sorting apparatus A will be described.

When the user starts analysis, the microparticle sorting apparatus A drives a pump to feed the sample fluid and the sheath fluid to the sample fluid inlet 11 and the sheath fluid inlet 13 of the microchip 1*a*. Consequently, a sheath flow in which the sample fluid laminar flow is sandwiched by the sheath fluid laminar flow is formed in the main channel 15.

The microparticles are fed to the detection area 15*a* in a single line arranged in the sheath flow, and are irradiated by the excitation light from the irradiation unit 21. Fluorescence and scattered light emitted from the microparticles due to the irradiation of excitation light are detected by the detection unit 22, and converted into an electric signal. The electric signal is output to the drive unit 23.

Figure 6:
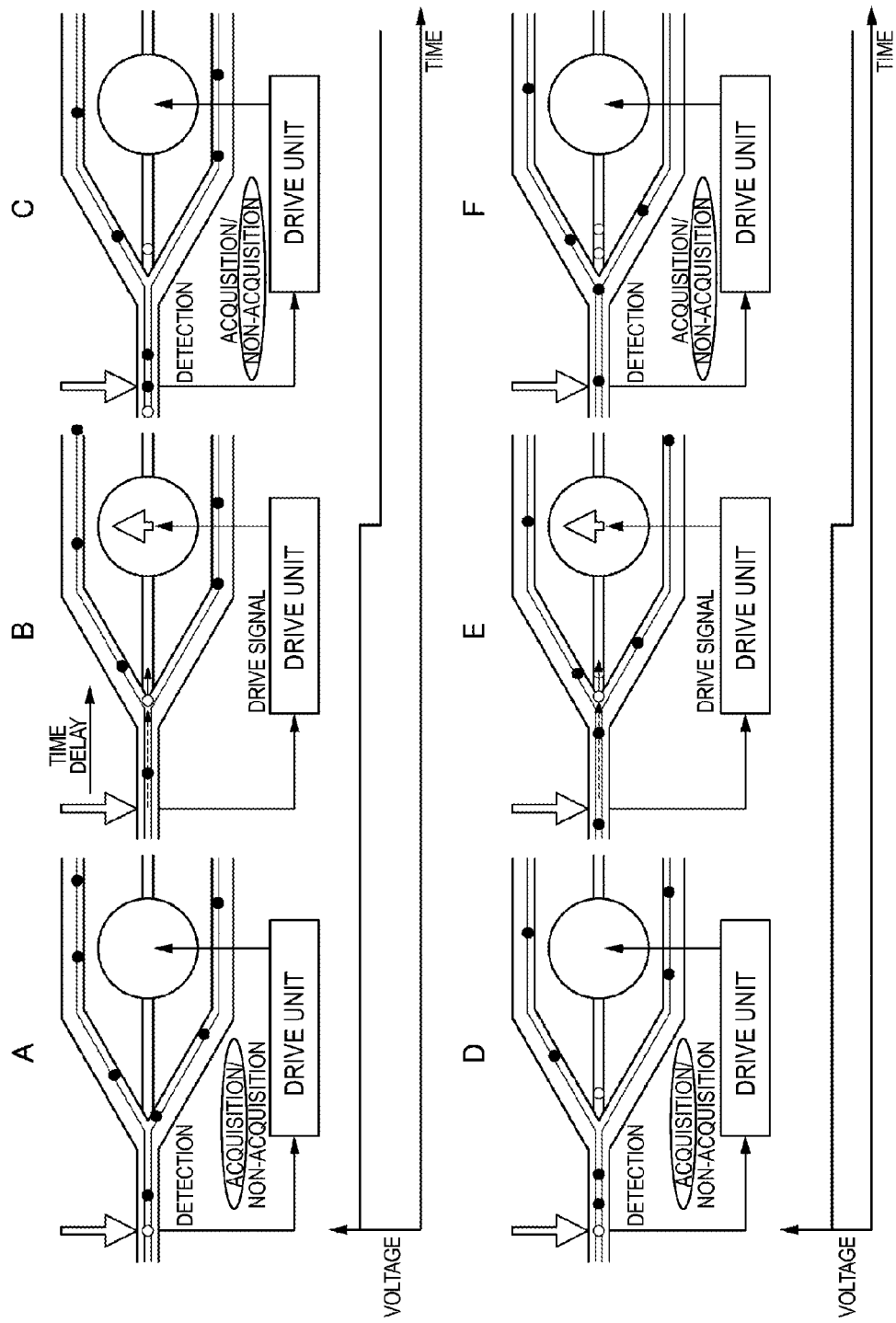
FIG. 6 is a diagram illustrating a sorting operation in the microparticle sorting apparatus A.
Figure 7:
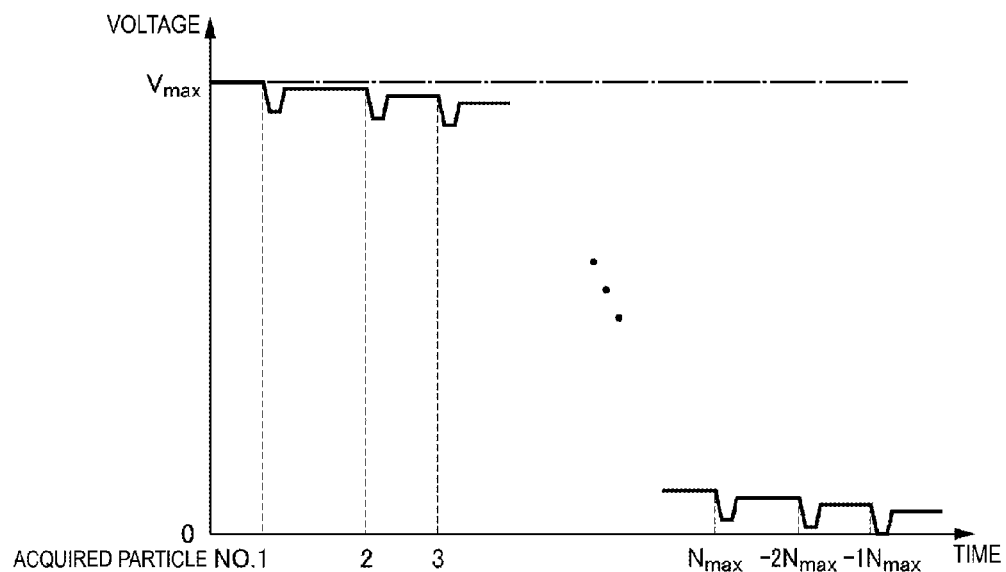
FIG. 7 is a diagram illustrating a voltage of an "undershoot-step waveform" applied from a drive unit 23 to an actuator 31 in the microparticle sorting apparatus A.

The drive unit 23 determines the optical characteristics of the microparticles based on the input electric signal. If a microparticle is determined to be a target particle, as illustrated in FIGS. 6A and B, after the time (delay period) that the target particle takes to move from the detection area 15*a* to the branching portion has elapsed, the drive unit 23 issues a drive signal to the actuator 31 for acquiring this microparticle. At this point, if necessary, the drive unit 23 can also be configured to drive the actuator 31 via an amplifier.

Specifically, if the actuator 31 is a piezo element, the drive unit 23 produces a negative pressure in the sorting channel 16 by applying a voltage that causes piezo contraction, which causes the volume of the pressure chamber 161 to increase, whereby the target particles collect in the sorting channel 16 from the main channel 15.

On the other hand, if it is determined that a microparticle is not a target particle, as illustrated in FIGS. 6C and D, the drive unit 23 issues a non-acquisition drive signal to the actuator 31, and performs optical characteristics determination of the next microparticle. It is noted that if the actuator 31 has received a non-acquisition drive signal, the actuator 31 does not operate.

The drive unit 23 repeats the optical characteristics determination of the microparticles and the output of a drive signal to the actuator 31 until analysis is finished (refer to FIGS. 6E and F), so that only the target particles accumulate in the sorting channel 16 (refer to FIG. 6F). After analysis has finished, the target particles that have been separated into the sorting channel 16 are recovered by the user.

[Drive Signal]

By referring to FIG. 7 to FIG. 10, the waveforms of the voltages to be applied from the drive unit 23 to the actuator 31 (the drive signals when acquiring the target particles) will be described. For increasing the volume of the pressure chamber 161 by the contraction of the actuator 31 to sequentially drawing the target particles into the sorting channel 16 by the negative pressure, the waveform is preferably the "undershoot-step waveform" illustrated in FIG. 7.

Figure 8:
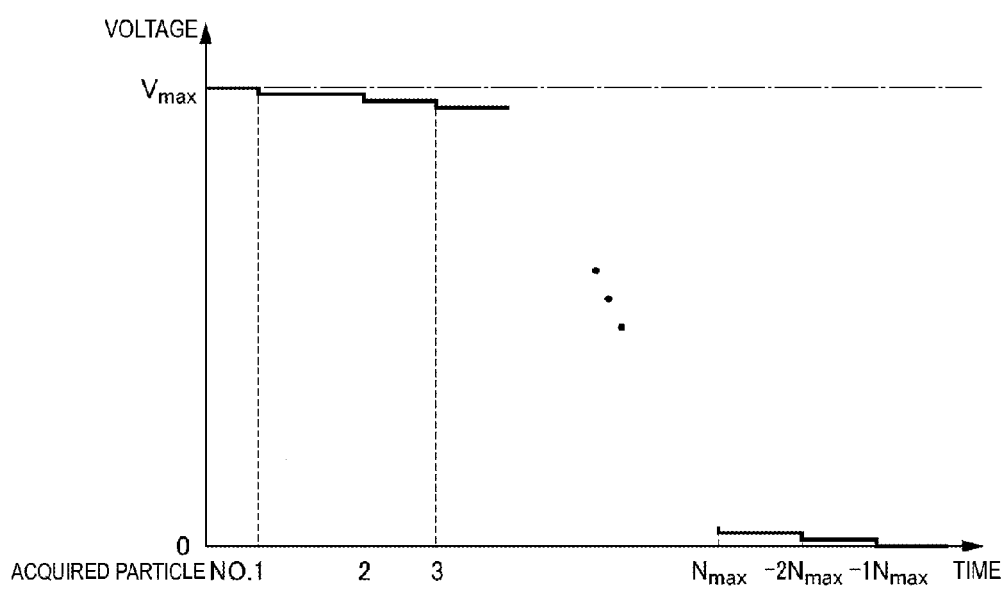
FIG. 8 is a diagram illustrating a voltage of a "step waveform" for comparison.
Figure 9:
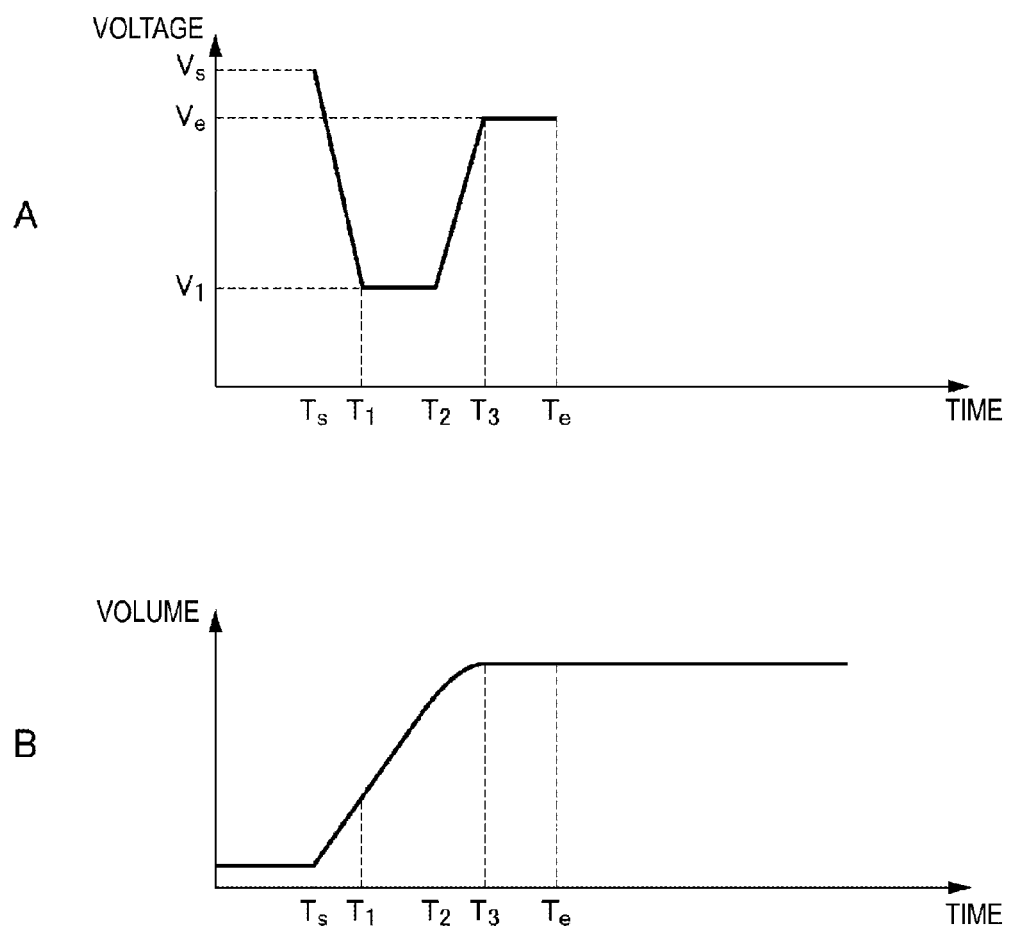
FIG. 9 is a diagram illustrating a change in voltage (A) with the "undershoot-step waveform" and a change in volume (B) of a fluid drawn into the sorting channel 16.
Figure 10:
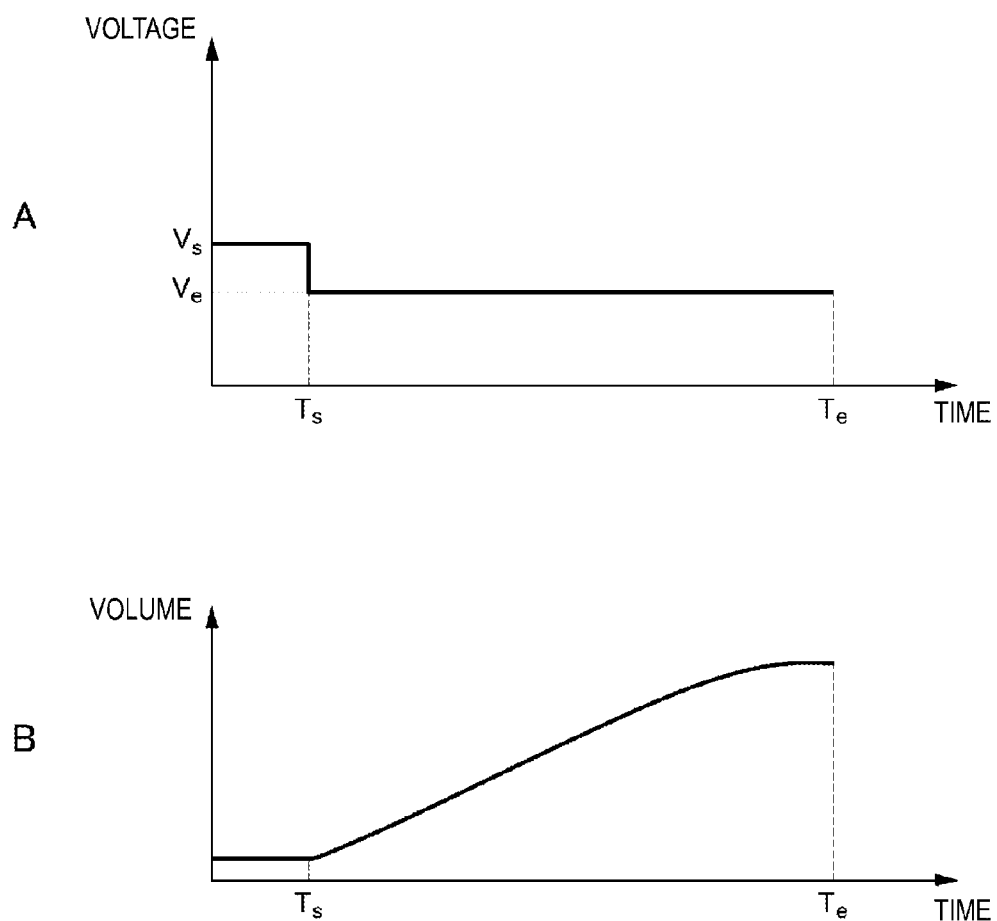
FIG. 10 is a diagram illustrating a change in voltage (A) with the "step waveform" and a change in volume (B) of a fluid drawn into the sorting channel 16 for comparison.

Here, the "undershoot-step waveform" means a waveform in which an undershoot portion having a voltage value lower than that in a step portion immediately after starting to issue a signal is added to the "step waveform" illustrated in FIG. 8.

More specifically, the "undershoot-step waveform" is a waveform in which, as illustrated in FIG. 9A, the voltage value significantly decreases from $V_s$ to $V_1$ during the period from start time $T_S$ to time $T_1$, and thereafter, the voltage recovers to a voltage value $V_e$ ($V_1 < V_e < V_s$) during the period to end time $T_e$. Here, the waveform is illustrated in which after the voltage value $V_1$ is maintained from time $T_1$ to time $T_2$; the voltage value increases from $V_1$ to $V_e$ over the period to time $T_3$; and the voltage value $V_e$ is maintained during the period to time $T_e$. On the other hand, the "step waveform" is a waveform in which, as illustrated in FIG. 10A, the voltage value decreases from $V_s$ to $V_e$ at start time $T_S$, and the voltage value $V_e$ ($V_1 < V_e$) is maintained during the period to end time $T_e$.

The voltage values of the undershoot-step waveform and the step waveform at start time $T_S$ are identical at $V_s$. Also, the voltage values of the undershoot-step waveform and the step waveform at the signal end $T_e$ are identical at $V_e$. Furthermore, the decrease range of the voltage value between the undershoot-step waveform and the step waveform in one waveform are identical at ($V_S-V_e$). The voltage range ($V_S-V_e$) is comparable to the piezo drive voltage necessary for drawing in one target particle into the sorting channel 16. On the other hand, in the undershoot-step waveform, the voltage value further significantly decreases down to $V_1$ ($V_1 < V_e$) during the period from immediately after time $T_s$ to time $T_3$, thereby allowing the temporary decrease range of the voltage value to become larger compared to the range in the step waveform.

FIG. 9B and FIG. 10B illustrate an increase in the volume of a fluid drawn into the sorting channel 16, when the voltages of the undershoot-step waveform and the step waveform are applied to the actuator 31. In the application of the voltage of the undershoot-step waveform (refer to FIG. 9B), a larger decrease range of the voltage during the period from immediately after time $T_s$ to time $T_3$ can be ensured compared to in the application of the voltage of the step waveform (refer to FIG. 10B). For this reason, with the undershoot-step waveform, a large contraction force can be generated in the actuator 31 immediately after starting to issue a signal (time $T_s$ to time $T_3$), thereby enabling the generation of a large negative pressure in the sorting channel 16. Consequently, with an undershoot-step waveform, immediately after starting to draw in the target particles, a response to the increase in the collection volume of the sample fluid and the sheath fluid inlet in the sorting channel 16 from the main channel 15 can be made more quickly, which enables the target particles to be collected more rapidly.

On the contrary, with the step waveform, the response to the increase in the volume of the sample fluid and the sheath fluid drawn into the sorting channel 16 is delayed due to an inertial force and resistance of the fluid. Due to this delay in the response to the increase, with the step waveform, a time taken for the collection becomes longer, and the collection of the target particles also becomes unstable.

For enabling the sorting operation to become faster, it is also conceivable to increase the decrease range ($V_s-V_e$) of the voltage value in the step waveform illustrated in FIG. 10A. However, when the sorting operation of the microparticles is performed in the larger decrease range ($V_s-V_e$), the voltage value of the actuator 31 becomes 0, and the actuator 31 reaches the limit of the movable range earlier. For this reason, the maximum number ($N_{max}$ in FIG. 8) of the microparticles that can be drawn into the sorting channel 16 comes to considerably decrease. On the contrary, with the undershoot-step waveform, the decrease in the number of microparticles that can be drawn in can be suppressed to be solely an amount derived from the voltage range ($V_e-V_1$) in one undershoot waveform.

As above, according to the microparticle sorting apparatus A, the actuator 31 is driven with the voltage of the undershoot-step waveform. Accordingly, only the target particles can be quickly and stably drawn into the sorting channel 16, to be sorted out from non-target particles. It is noted that the non-target particles that have flowed to the waste channel 17 may be accumulated in the waste channel 17 or be externally discharged.

3. Configuration of the Microparticle Sorting Apparatus and the Microchip for Sorting Microparticles According to the Second Embodiment

[Microchip Configuration]

Figure 11:
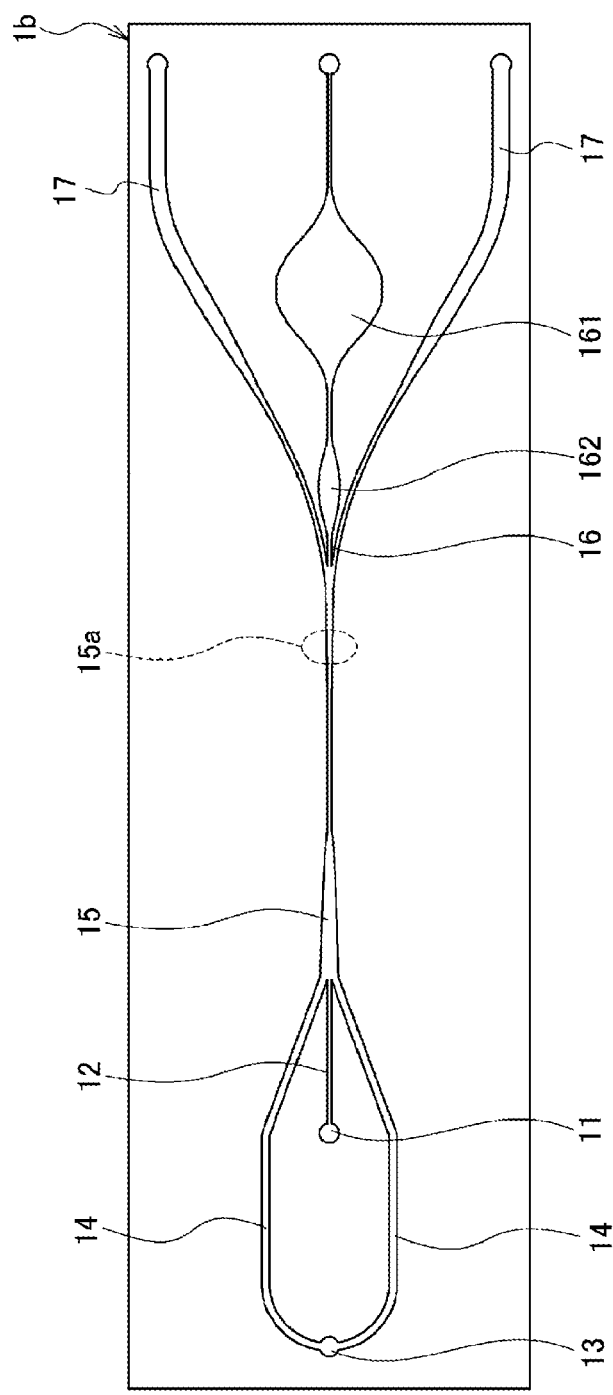
FIG. 11 is a diagram illustrating a configuration of a microchip 1b that is mounted on a microparticle sorting apparatus B according to the second embodiment of the present technology.
Figure 12:
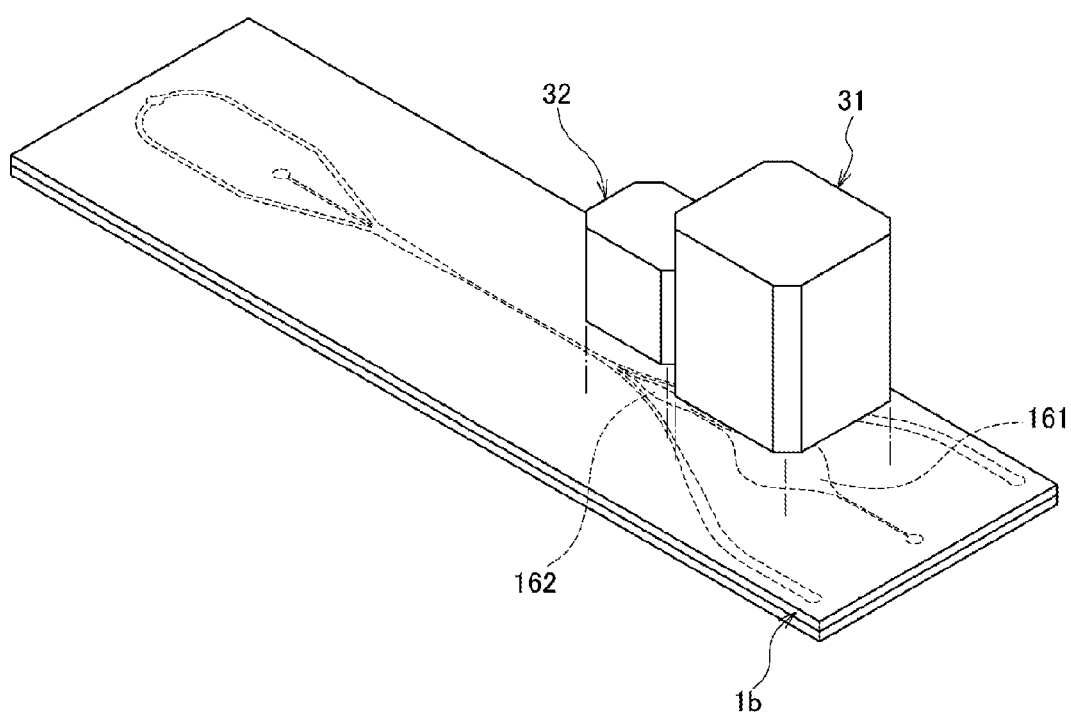
FIG. 12 is a diagram illustrating a configuration of the microchip 1b.

FIG. 11 and FIG. 12 are each a diagram illustrating a configuration of a microchip 1b that is mounted on a microparticle sorting apparatus B according to the second embodiment of the present technology. FIG. 11 is a top view; and FIG. 12 is a perspective view.

The microchip 1b differs from the microchip 1a according to the first embodiment, in terms of including a pressure chamber 162 in the sorting channel 16. The microchip 1b has the pressure chamber 161 and the pressure chamber 162 both arranged in series in the sorting channel 16. The pressure chamber 162 is also formed as an area whose inner space has expanded in the sorting channel 16, in a similar manner to the pressure chamber 161 (refer to FIGS. 11).

An actuator 32 is arranged on the surface of the microchip 1b corresponding to the pressure chamber 162 (refer to FIG. 12). The actuator 32 also functions in a similar manner to the actuator 31, to provide the surface (contact surface) of the microchip 1b with a stretching force, thereby causing a change in pressure within the sorting channel 16. The configuration other than the pressure chamber 162 and the actuator 32 of the microchip 1b is similar to the configuration in the microchip 1a.

[Whole Configuration of Apparatus]

The microparticle sorting apparatus B includes a microchip 1b, an irradiation unit 21, a detection unit 22, and a drive unit 23. Of these, the configuration of the irradiation unit 21 and the detection unit 22 is similar to the configuration of the microparticle sorting apparatus A according to the first embodiment.

In the microparticle sorting apparatus B, the drive unit 23 determines the optical characteristics of microparticles based on an electric signal input from the detection unit 22, and controls a voltage applied to the actuators 31 and 32 based on the determination result.

4. Operation of the Microparticle Sorting Apparatus According to the Second Embodiment

[Drive Signal]

Next, the operation of the microparticle sorting apparatus B will be described. Of the operation of the microparticle sorting apparatus B, an operation such as forming the sheath flow before reaching the sorting operation of the microparticles, and detecting and determining the optical characteristics of the microparticles is similar to the operation of the microparticle sorting apparatus A.

Figure 13:
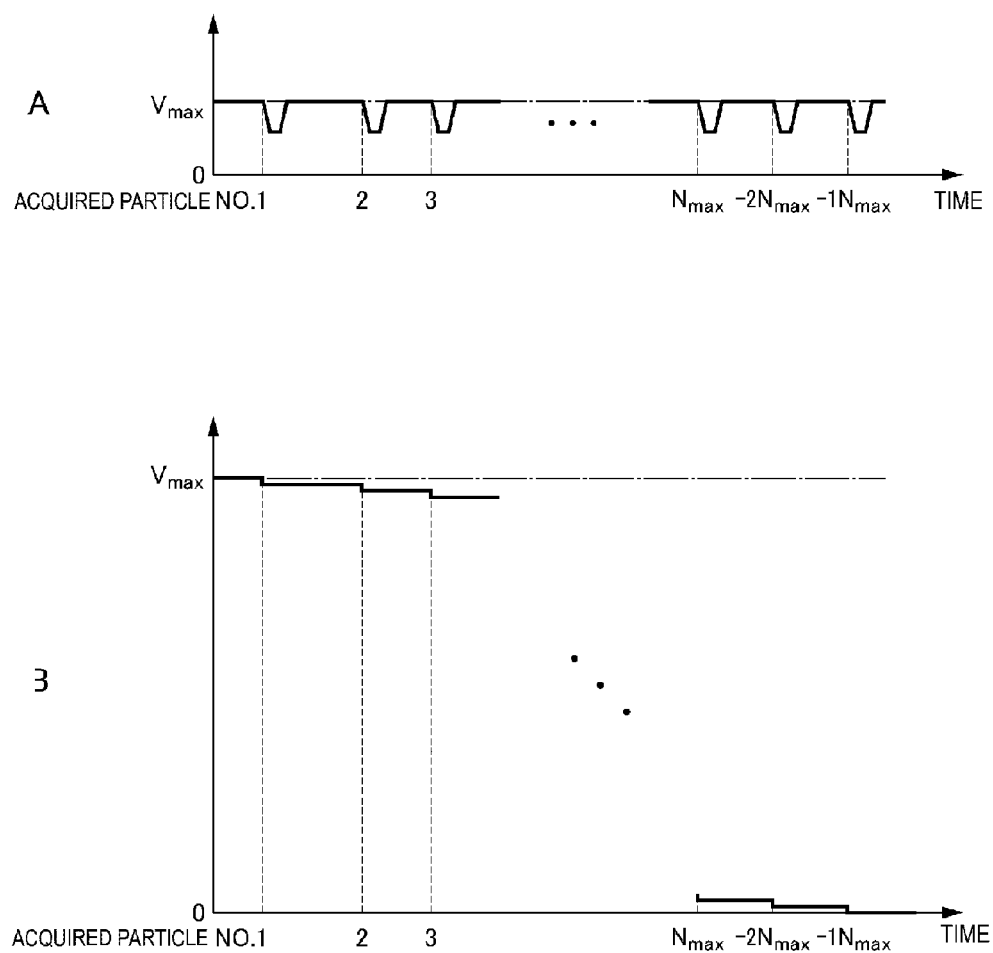
FIG. 13 is a diagram illustrating a "pulse waveform" (A) to be applied to an actuator 32 and a "step waveform" (B) to be applied to the actuator 31, from the drive unit 23 in the microparticle sorting apparatus B.

In the microparticle sorting apparatus B, the drive unit 23 also issues the drive signal to the actuator 32 in addition to the actuator 31 for acquiring the target particles. At this time, the drive unit 23 applies the voltage of the "pulse waveform" illustrated in FIG. 13A to the actuator 32, and applies the voltage of the step waveform illustrated in FIG. 13B to the actuator 31.

Figure 14:
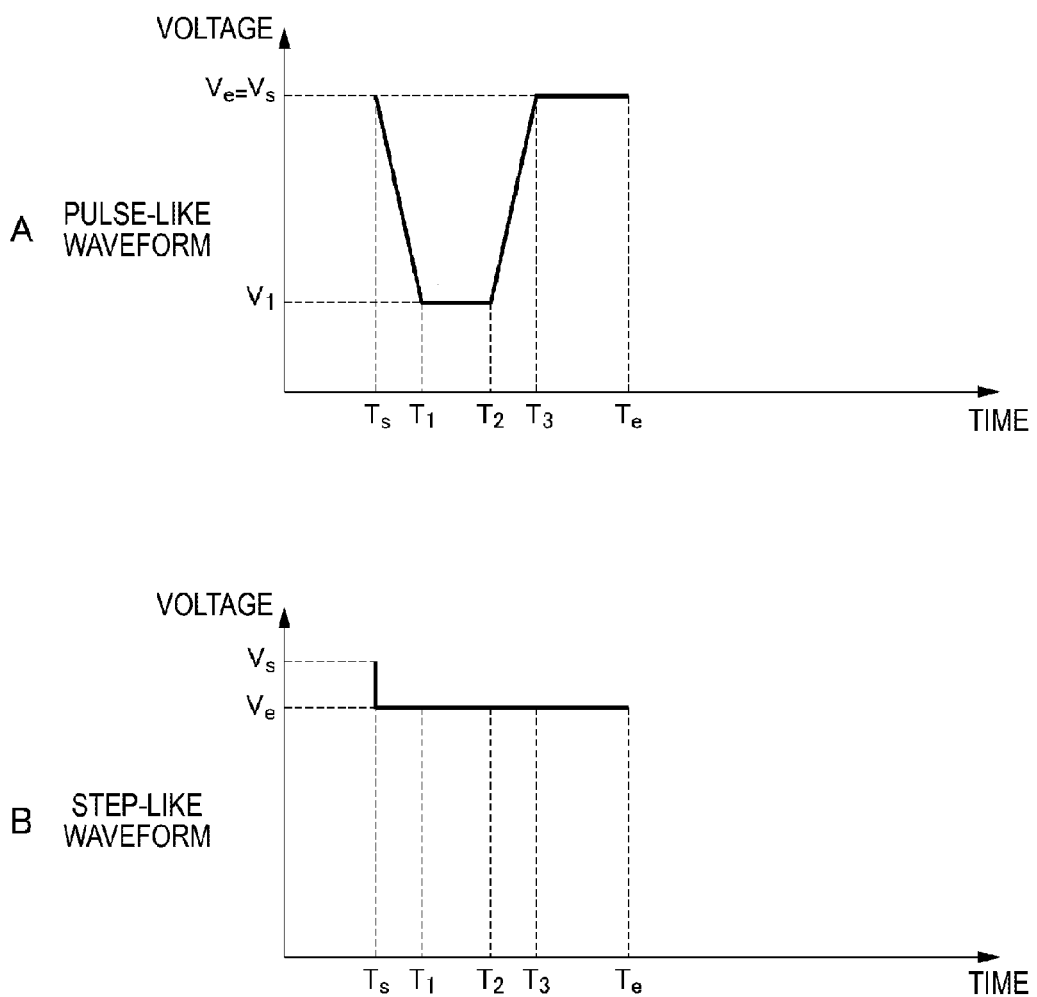
FIG. 14 is a diagram illustrating a change in voltage (A) with the "pulse waveform" and a change in voltage (B) with the "step waveform".

As described herein, the "pulse waveform" is a waveform in which, as illustrated in FIG. 14A, the voltage value significantly decreases from $V_s$ to $V_1$ during the period from signal start time $T_S$ to time $T_1$, and thereafter, the voltage recovers from $V_1$ to $V_e$ ($V_e$=$V_s$) during the period from time $T_2$ to time $T_3$. Here, the waveform is illustrated in which the voltage value $V_1$ is maintained from time $T_1$ to time $T_2$, and the voltage value $V_e$ is maintained from time $T_3$ to end time $T_e$. In FIG. 14B, the "step waveform" is illustrated.

The voltage values of the pulse waveform and the step waveform at start time $T_S$ are identical at $V_s$. However, while the voltage value of the step waveform at end time $T_e$ is $V_e$ ($V_e$<$V_s$), the voltage value of the pulse waveform at end time $T_e$ recovers to $V_e$ ($V_e$=$V_s$). For this reason, while the voltage value decreases by ($V_S$-$V_e$) in one waveform in the step waveform, the voltage value do not decrease in the pulse waveform.

The drive unit 23 generates a signal of the "undershoot-step waveform" by synthesis between the signal of the pulse waveform applied to the actuator 32 and the signal of the step waveform applied to the actuator 31. Accordingly, the drive unit 23 causes a change in pressure containing the step waveform component and the undershoot waveform component within the sorting channel 16.

In the sorting operation by the synthesis between the pulse waveform and the step waveform, firstly, the voltage of the step waveform applied to the actuator 31 causes the volume of the pressure chamber 161 to increase by an amount necessary for drawing in the target particles. In addition to this, the volume of the pressure chamber 162 significantly increases with the voltage of the pulse waveform applied to the actuator 32 immediately after starting to issue a signal (time $T_s$ to time $T_3$). Consequently, the collection volume of the sample fluid and the sheath fluid inlet in the sorting channel 16 can be significantly increased immediately after starting to draw in the target particles, while finally becoming only the volume necessary for drawing in the target particles. For this reason, according to the sorting operation by the synthesis between the pulse waveform and the step waveform, the target particles can be quickly drawn in, in a similar manner to the case of the above-described undershoot-step waveform.

Furthermore, the sorting operation by the synthesis between the pulse waveform and the step waveform can inhibit the decrease in the number of microparticles that can be drawn in derived from the voltage range ($V_e$-$V_1$) in one undershoot waveform, which can be caused by the sorting operation with the undershoot-step waveform.

In the microparticle sorting apparatus B, the drive signal to the actuator 32 may be the pulse waveform while the drive signal to the actuator 31 may be the undershoot-step waveform instead of the step waveform. In this case, a further larger negative pressure can be generated within the sorting channel 16 immediately after starting to draw in the target particles, thereby enabling a further faster drawing-in operation.

Also, in the microparticle sorting apparatus B, the actuator 32 to be applied with the voltage of the pulse waveform needs to be arranged corresponding to the pressure chamber 162 that is located close to the communication opening to the main channel 15. If the actuator 32 to be driven with the pulse waveform is arranged to the pressure chamber 161 while the actuator 31 to be driven with the step waveform or the undershoot-step waveform is arranged to the pressure chamber 162, the target particles that are temporarily drawn into the sorting channel 16 can be discharged back into the main channel 15.

5. Configuration of the Microparticle Sorting Apparatus and the Microchip for Sorting Microparticles According to the Third Embodiment

[Microchip Configuration]

Figure 15:
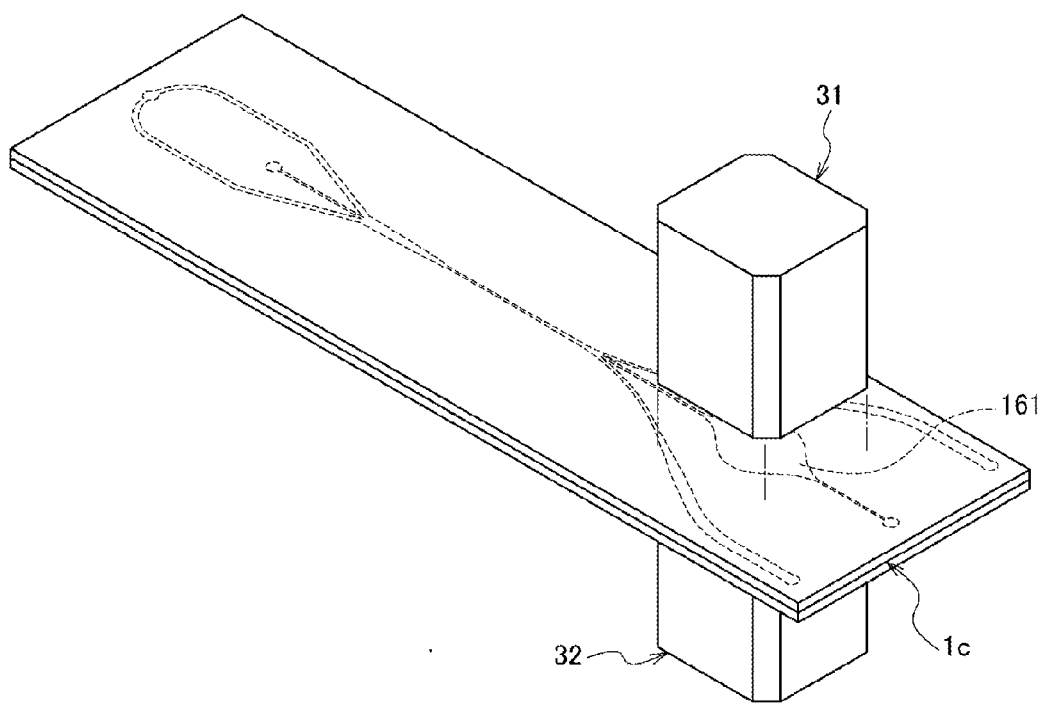
FIG. 15 is a diagram illustrating a configuration of a microchip 1c that is mounted on a microparticle sorting apparatus C according to the third embodiment of the present technology.
Figure 16:
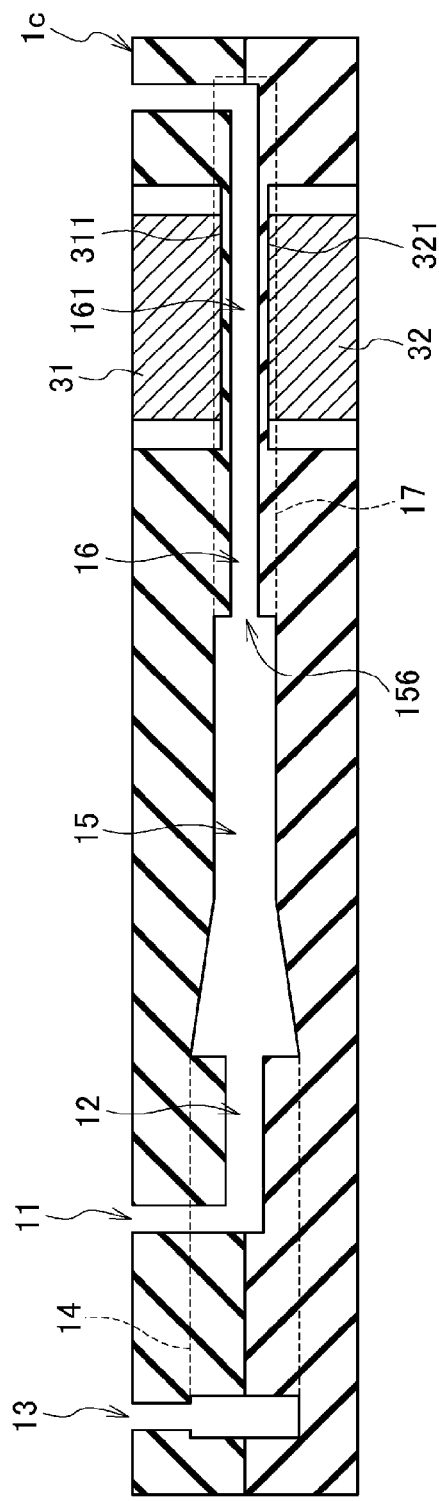
FIG. 16 is a diagram illustrating a configuration of the microchip 1c.

FIG. 15 and FIG. 16 are each a diagram illustrating a configuration of a microchip 1c that is mounted on a microparticle sorting apparatus C according to the third embodiment of the present technology. FIG. 15 is a perspective view, and FIG. 16 is a cross-sectional view.

The microchip 1c differs from the microchip 1a according to the first embodiment, in terms of including the actuator 32 at a position corresponding to the pressure chamber 161. The microchip 1c has the actuator 31 on one surface and the actuator 32 on the back surface, with respect to the pressure chamber 161 (refer to FIG. 15).

The actuator 32 is arranged in contact with a displacement plate 321 that is formed by creating a recess on the back surface of the microchip 1c at the position corresponding to the pressure chamber 161 (refer to FIG. 16). The actuator 32 also functions in a similar manner to the actuator 31, so as to expand and contract as the applied voltage changes, causing the change in pressure within the pressure chamber 161 via the displacement plate 321. The configuration other than the actuator 32 and the displacement plate 321 of the microchip 1c is similar to the configuration of the microchip 1a.

[Whole Configuration of Apparatus]

The microparticle sorting apparatus C includes a microchip 1c, an irradiation unit 21, a detection unit 22, and a drive unit 23. Of these, the configuration of the irradiation unit 21 and the detection unit 22 is similar to the configuration of the microparticle sorting apparatus A according to the first embodiment.

In the microparticle sorting apparatus C, the drive unit 23 determines the optical characteristics of microparticles based on an electric signal input from the detection unit 22, and controls a voltage applied to the actuators 31 and 32 based on the determination result.

6. Operation of the Microparticle Sorting Apparatus According to the Third Embodiment

[Drive Signal]

Next, the operation of the microparticle sorting apparatus C will be described. Of the operation of the microparticle sorting apparatus C, an operation such as forming the sheath flow before reaching the sorting operation of the microparticles, and detecting and determining the optical characteristics of the microparticles is similar to the operation of the microparticle sorting apparatus A.

In the microparticle sorting apparatus C, the drive unit 23 also issues the drive signal to the actuator 32 in addition to the actuator 31 for acquiring the target particles. At this time, the drive unit 23 applies the voltage of the "pulse waveform" illustrated in FIG. 13A to the actuator 32, and applies the voltage of the step waveform illustrated in FIG. 13B to the actuator 31.

The drive unit 23 generates a signal of the "undershoot-step waveform" by synthesis between the signal of the pulse waveform applied to the actuator 32 and the signal of the step waveform applied to the actuator 31. Accordingly, the drive unit 23 causes the change in pressure containing the step waveform component and the undershoot waveform component within the sorting channel 16.

In the sorting operation by the synthesis between the pulse waveform and the step waveform, the actuator 31 driven by the step waveform causes the volume of the pressure chamber 161 to increase by an amount necessary for drawing in the target particles. In addition to this, the actuator 32 driven by the pulse waveform causes a large negative pressure to be generated in the pressure chamber 161 immediately after starting to issue the signal (time $T_s$ to time $T_3$ in FIG. 14A). Accordingly, although the collection volume of the sample fluid and the sheath fluid inlet in the sorting channel 16 finally becomes only the volume necessary for drawing in the target particles, the volume comes to significantly increase immediately after starting to draw in the target particles. For this reason, according to the sorting operation by the synthesis between the pulse waveform and the step waveform, the target particles can be quickly drawn in, in a similar manner to the case of the above-described undershoot-step waveform.

In the microparticle sorting apparatus C, the drive signal to the actuator 32 may be the pulse waveform while the drive signal to the actuator 31 may be the undershoot-step waveform instead of the step waveform. In this case, a further larger negative pressure can be generated within the pressure chamber 161 immediately after starting to draw in the target particles, thereby enabling a further faster drawing-in operation.

7. Configuration of the Microparticle Sorting Apparatus and the Microchip for Sorting Microparticles According to the Fourth Embodiment

[Microchip Configuration]

Figure 17:
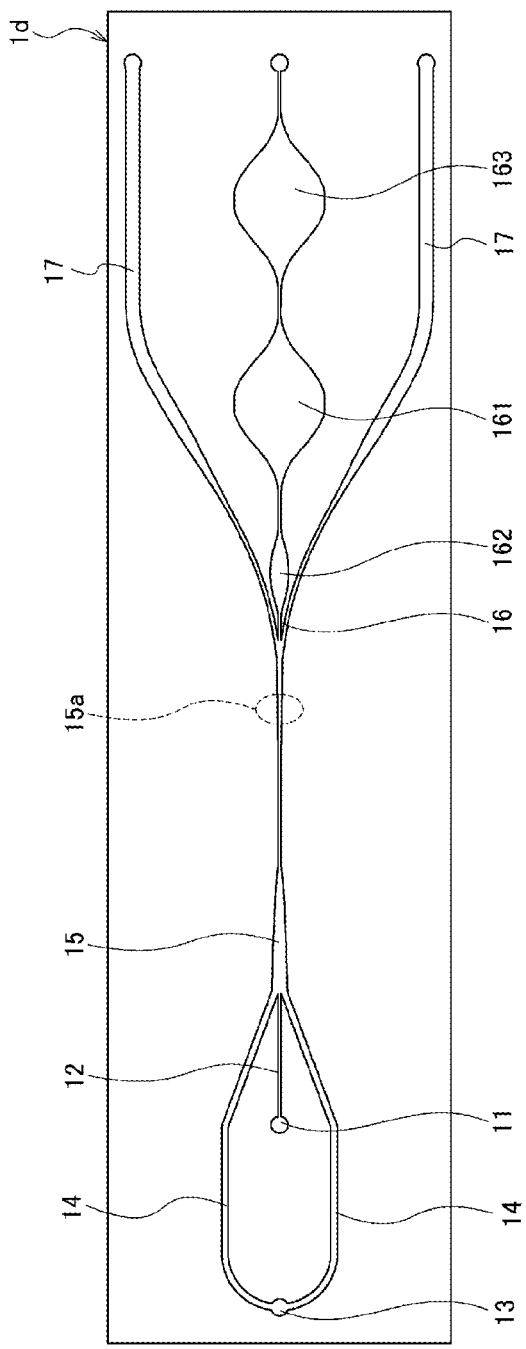
FIG. 17 is a diagram illustrating a configuration of a microchip 1d that is mounted on a microparticle sorting apparatus D according to the fourth embodiment of the present technology.

FIG. 17 is a diagram illustrating a configuration of a microchip 1d that is mounted on a microparticle sorting apparatus D according to the fourth embodiment of the present technology.

The microchip 1d differs from the microchip 1b according to the second embodiment, in terms of including a pressure chamber 163 in the sorting channel 16. In the microchip 1b, the pressure chamber 161, the pressure chamber 162 and the pressure chamber 163 are arranged in series in the sorting channel 16. The pressure chamber 163 is also formed as an area whose inner space has expanded in the sorting channel 16, in a similar manner to the pressure chambers 161 and 162.

An actuator is arranged on the surface of the microchip 1d corresponding to the pressure chamber 163. This actuator, which is not illustrated, will be described as an "actuator 33". The actuator 33 also functions in a similar manner to the actuators 31 and 32, so as to provide displacement to the surface (contact surface) of the microchip 1d to change the volume within the pressure chamber 163, thereby causing the change in pressure within the sorting channel 16. The configuration other than the pressure chamber 163 and the actuator 33 of the microchip 1d is similar to the configuration of the microchip 1b.

[Whole Configuration of Apparatus]

The microparticle sorting apparatus D includes a microchip 1d, an irradiation unit 21, a detection unit 22, and a drive unit 23. Of these, the configuration of the irradiation unit 21 and the detection unit 22 is similar to the configuration of the microparticle sorting apparatus A according to the first embodiment.

In the microparticle sorting apparatus D, the drive unit 23 determines the optical characteristics of microparticles based on an electric signal input from the detection unit 22, and controls a voltage applied to the actuator 31, 32 and 33 based on the determination result.

8. Operation of the Microparticle Sorting Apparatus According to the Fourth Embodiment

[Drive Signal]

Next, the operation of the microparticle sorting apparatus D will be described. Of the operation of the microparticle sorting apparatus D, an operation such as forming the sheath flow before reaching the sorting operation of the microparticles, and detecting and determining the optical characteristics of the microparticles is similar to the operation of the microparticle sorting apparatus A.

In the microparticle sorting apparatus D, the drive unit 23 also issues the drive signal to the actuator 33 in addition to the actuators 31 and 32 for acquiring the target particles. At this time, the drive unit 23 applies the voltage of the "pulse waveform" illustrated in FIG. 18A to the actuator 32, and applies the voltages of the step waveforms illustrated in FIGS. 18B and 18C to the actuators 31 and 33.

The drive unit 23 generates a signal of the "undershoot-step waveform" by synthesis between the signal of the pulse waveform applied to the actuator 32 and the signal of the step waveform applied to the actuator 31. Accordingly, the drive unit 23 causes the change in pressure containing the step waveform component and the undershoot waveform component within the sorting channel 16, thereby performing the sorting of the target particles.

Furthermore, when the movable range of the actuator 31 reaches the limit, causing the voltage value applied to the actuator 31 to become 0, the drive unit 23 starts signal output to the actuator 33. Consequently, the drive unit 23 generates a signal of the undershoot-step waveform by the synthesis between the signal of the step waveform applied to the actuator 33 and the signal of the pulse waveform applied to the actuator 32, thereby continuing the sorting of the target particles.

Thus, by starting to drive another new actuator, in place of the actuator having reached the limit of the movable range, so as to continue the sorting operation, the maximum number of microparticles that can be drawn into the sorting channel 16 can be increased.

In the microparticle sorting apparatus D, the combinations of the actuator and the pressure chamber are not limited to three illustrated herein, and four or more combinations may be arranged. For example, when two or more combinations of the actuator to be driven by the pulse waveform and the pressure chamber are arranged, a larger negative pressure can be generated within the sorting channel 16 immediately after starting to draw in the target particles, thereby enabling a further faster drawing-in operation. Also, when three or more combinations of the actuator to be driven by the step waveform and the pressure chamber are arranged, these three or more combinations are sequentially driven, thereby further increasing the maximum number of microparticles that can be drawn into the sorting channel 16.

Also, in the microparticle sorting apparatus D, the drive signal to the actuator 32 may be the pulse waveform while the drive signals to the actuators 31 and 33 may be the undershoot-step waveforms instead of the step waveforms. In this case, a further larger negative pressure can be generated within the sorting channel 16 immediately after starting to draw in the target particles, thereby enabling a further faster drawing-in operation.

It is noted that in the microparticle sorting apparatus D, the actuator 32 to be applied with the voltage of the pulse waveform also needs to be arranged corresponding to the pressure chamber 162 that is located close to the communication opening to the main channel 15. If the actuator 32 to be driven by the pulse waveform is arranged to the pressure chamber 161 or the pressure chamber 163, the target particles that are temporarily drawn into the sorting channel 16 can be discharged back into the main channel 15.

9. Microparticle Sorting Method and Microparticle Sorting Program

A microparticle sorting method according to an embodiment of the present technology corresponds to the operation executed by the drive unit 23 of the above-described microparticle sorting apparatuses. Also, a microparticle sorting program for executing this operation is stored in the drive unit 23 of the microparticle sorting apparatuses.

The program is stored on a hard disk, read into a memory under the control of the CPU and OS, and executes the above-described sorting operation. The program can be recorded on a computer-readable recording medium. The recording medium may be any recording medium as long as it is a computer-readable recording medium. Specifically, a disk-shaped recording medium may be used, such as a flexible disk and a CM-ROM. Further, a tape type recording medium may be used, such as a magnetic tape. In addition, a configuration can also be employed in which a part of the processing may be configured from hardware, such as a DSP (digital signal processor), an ASIC (application specific integrated circuit), a PLD (programing logic device), and a FPGA (field-programmable gate array), and high-speed processing is performed in cooperation with the above-described software program.

Additionally, the present technology may also be configured as below.

(1)
A microparticle sorting apparatus, including:
a main channel through which a fluid including microparticles flows;
a branch channel that is in communication with the main channel;
an actuator that causes a negative pressure to be generated in the branch channel; and
a drive unit that controls a voltage applied to the actuator to cause a change in pressure containing a step waveform component and an undershoot waveform component in the branch channel.

(2)
The microparticle sorting apparatus according to (1), including two or more of the actuators,
wherein the drive unit applies the voltage of a pulse waveform to one or more of the actuators, while applying the voltage of a step waveform to other one or more of the actuators.

(3)
The microparticle sorting apparatus according to (2), wherein the drive unit applies the voltage of the pulse waveform to one or more of the actuators, while applying the voltage of an undershoot-step waveform to other one or more of the actuators.

(4)
The microparticle sorting apparatus according to any one of (1) to (3),
wherein the main channel and the branch channel are formed inside a microchip, and
wherein the actuator is arranged in contact with a surface of the microchip at a position corresponding to the branch channel.

(5)
The microparticle sorting apparatus according to (4), wherein the actuator provides displacement to a contact surface of the microchip.

(6)
The microparticle sorting apparatus according to (5), wherein a portion of the branch channel corresponding to an arrangement position of the actuator is configured as a pressure chamber where a change in volume is caused by the displacement.

(7)
The microparticle sorting apparatus according to any one of (2) to (6),
wherein in the branch channel, the pressure chambers are arranged in series, and
wherein the actuator to be applied with the voltage of the pulse waveform is arranged corresponding to the pressure chamber that is located closer to a communication opening to the main channel, than the actuator to be applied with the voltage of the step waveform or the undershoot-step waveform.

(8)
The microparticle sorting apparatus according to any one of (2) to (6), wherein the actuator to be applied with the voltage of the pulse waveform is arranged on one surface of the microchip, and the actuator to be applied with the voltage of the step waveform or the undershoot-step waveform is arranged on the opposite surface, with respect to one of the pressure chamber.

(9)
The microparticle sorting apparatus according to (1), wherein the drive unit applies a voltage of an undershoot-step waveform to the actuator.

REFERENCE SIGNS LIST

A microparticle sorting apparatus
S sample fluid laminar flow
T sheath fluid laminar flow
1*a*, 1*b*, 1*c*, 1*d* microchip
11 sample fluid inlet
12 sample fluid channel
13 sheath fluid inlet
14 sheath fluid channel
15 main channel
15*a* detection area
156 communication opening
16 sorting channel
161, 162, 163 pressure chamber
17 waste channel
21 irradiation unit
22 detection unit
23 drive unit
31, 32, 33 actuator
311, 321 displacement plate

The invention claimed is:
1. A microparticle sorting apparatus, comprising:
a main channel through which a fluid including microparticles flows;

a branch channel that is in communication with the main channel;

a first actuator and a second actuator that cause a negative pressure to be generated in the branch channel, wherein the first actuator and the second actuator are arranged opposite to each other at a position corresponding to the branch channel, and a drive unit configured to apply different voltages to the first actuator and second actuator to cause a change in pressure in the branch channel, wherein the drive unit is configured to apply a voltage of a pulse waveform to one of the first actuator and the second actuator, while applying a voltage of a step waveform to other of the first actuator and the second actuator.

2. The microparticle sorting apparatus according to claim 1, wherein the drive unit is configured to apply the voltage of the pulse waveform to one of the first and second actuators, while applying the voltage of an undershoot-step waveform to other of the first and second actuators.

3. The microparticle sorting apparatus according to claim 1,
wherein the main channel and the branch channel are formed inside a microchip, and
wherein the first and second actuators are arranged in contact with a surface of the microchip at a position corresponding to the branch channel.

4. The microparticle sorting apparatus according to claim 3, wherein the first and second actuators provide displacement to a contact surface of the microchip.

5. The microparticle sorting apparatus according to claim 4, wherein a portion of the branch channel corresponding to an arrangement position of the first and second actuators is configured as a pressure chamber where a change in volume is caused by the displacement.

6. The microparticle sorting apparatus according to claim 5,
wherein in the branch channel, a plurality of pressure chambers are arranged in series, and
wherein the one of the first and second actuators to be applied with the voltage of the pulse waveform is arranged corresponding to a pressure chamber among the plurality of pressure chambers that is located closer to a communication opening to the main channel, than the other of the first and second actuators to be applied with the voltage of the step waveform or the undershoot-step waveform.

7. The microparticle sorting apparatus according to claim 5, wherein one of the first and second actuators to be applied with the voltage of the pulse waveform is arranged on one surface of the microchip, and other of the first and second actuators to be applied with the voltage of the step waveform or the undershoot-step waveform is arranged on the opposite surface, with respect to the pressure chamber.

8. The microparticle sorting apparatus according to claim 1, wherein the drive unit is configured to apply a voltage of an undershoot-step waveform to one of the first and second actuators.

9. A microchip for sorting microparticles,
wherein a main channel through which a fluid including microparticles flows, and a branch channel that is in communication with the main channel are formed inside the microchip,
wherein a first actuator and a second actuator that provide displacement on a contact surface, using a drive unit, are arranged opposite to each other at a position corresponding to the branch channel, and
wherein one of the first actuator and the second actuator is applied with a voltage of a pulse waveform using the drive unit, while other of the first actuator and the second actuator is applied with a voltage of a step waveform using the drive unit.

10. The microchip for sorting microparticles according to claim 9, wherein the branch channel includes a pressure chamber where a change in volume is caused by the displacement.

11. The microchip for sorting microparticles according to claim 10, further comprising a plurality of combinations of the pressure chamber and the first and second actuators.

12. The microchip for sorting microparticles according to claim 10, wherein
the first actuator is arranged on one surface of the microchip,
the second actuator is arranged on a surface opposite to the one surface of the microchip, and
the first and second actuators are arranged on the microchip with respect to the pressure chamber.

13. A microparticle sorting method, comprising:
generating a negative pressure within a branch channel that is in communication with a main channel, to draw, into the branch channel, microparticles included in a fluid that flows through the main channel,
wherein in the microparticle sorting method, different voltages are applied to a first actuator and a second actuator to cause a change in pressure in the branch channel, wherein the first actuator and second actuator are arranged opposite to each other at a position corresponding to the branch channel, and
wherein in the microparticle sorting method, a voltage of a pulse waveform is applied to one of the first actuator and the second actuator, while a voltage of a step waveform is applied to other of the first actuator and the second actuator.

14. The microparticle sorting method according to claim 13, wherein in the microparticle sorting method, a change in pressure of an undershoot-step waveform is caused within the branch channel.

15. The microparticle sorting method according to claim 13, wherein in the microparticle sorting method,
determining, at a detection area, whether the microparticles in the fluid satisfy predetermined optical characteristics; and
collecting the microparticles that satisfy the predetermined optical characteristics.

* * * * *